(12) United States Patent
Narkiss et al.

(10) Patent No.: US 10,660,579 B2
(45) Date of Patent: May 26, 2020

(54) SYSTEMS AND METHODS FOR OPERATING AN ALERT SYSTEM OF MEDICAL DEVICES

(71) Applicant: ORIDION MEDICAL 1987 LTD., Jerusalem (IL)

(72) Inventors: Nadav Narkiss, Beer Yaakov (IL); Moshe Tal, Efrat (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 0 days.

(21) Appl. No.: 16/123,117

(22) Filed: Sep. 6, 2018

(65) Prior Publication Data

US 2019/0076100 A1 Mar. 14, 2019

Related U.S. Application Data

(60) Provisional application No. 62/558,715, filed on Sep. 14, 2017.

(51) Int. Cl.
G08B 21/00 (2006.01)
A61B 5/00 (2006.01)
(Continued)

(52) U.S. Cl.
CPC .............. *A61B 5/746* (2013.01); *A61B 5/021* (2013.01); *A61B 5/02055* (2013.01); *A61B 5/02405* (2013.01); *A61B 5/0402* (2013.01); *A61B 5/0836* (2013.01); *A61B 5/6844* (2013.01); *A61B 5/70* (2013.01); *A61M 16/06* (2013.01); *A61M 16/0672* (2014.02); *A61B 5/002* (2013.01); *A61B 5/01* (2013.01); *A61B 5/053* (2013.01); *A61B 5/1455* (2013.01); *A61B 5/7465* (2013.01); *A61B 2562/0257* (2013.01); *A61M 16/085* (2014.02); *A61M 2005/006* (2013.01); *A61M 2205/13* (2013.01);
(Continued)

(58) Field of Classification Search
CPC .......................... A61B 5/746; A61M 16/0051
USPC ..... 340/686.1, 540, 541, 435, 438; 600/310, 600/323, 334, 335
See application file for complete search history.

(56) References Cited

U.S. PATENT DOCUMENTS 7,115,097 B2 * 10/2006 Johnson ............ A61M 16/0051
600/538
9,668,927 B2 * 6/2017 Campbell ................ A61G 5/10
(Continued)

FOREIGN PATENT DOCUMENTS

WO 2016042504 A1 3/2016

OTHER PUBLICATIONS

International Search Report and Written Opinion from PCT Application No. PCT/IL2018/050997 dated Dec. 13, 2018; 18 pgs.

*Primary Examiner* — Tai T Nguyen
(74) *Attorney, Agent, or Firm* — Cantor Colburn LLP

(57) ABSTRACT

A system for a medical system includes a position sensing unit to sense a displacement of a medical device from a medically operational point on a subject, and a signal processing circuit to output, based on the sensed displacement, a signal to disable an alert system when the medical device is for sensing a physiological parameter of a subject during a medical procedure and the displacement is greater than a first threshold value, or to output a signal to enable the alert system when the medical device is for delivering treatment to the subject and the displacement is greater than a second threshold value.

20 Claims, 9 Drawing Sheets

(51) Int. Cl.

| | |
|---|---|
| *A61B 5/083* | (2006.01) |
| *A61B 5/024* | (2006.01) |
| *A61B 5/0205* | (2006.01) |
| *A61B 5/021* | (2006.01) |
| *A61B 5/0402* | (2006.01) |
| *A61M 16/06* | (2006.01) |
| *A61M 5/00* | (2006.01) |
| *A61B 5/1455* | (2006.01) |
| *A61B 5/01* | (2006.01) |
| *A61M 16/08* | (2006.01) |
| *A61B 5/053* | (2006.01) |

(52) U.S. Cl.
CPC . *A61M 2205/18* (2013.01); *A61M 2205/3306* (2013.01); *A61M 2205/3368* (2013.01); *A61M 2205/3561* (2013.01); *A61M 2205/3592* (2013.01); *A61M 2205/50* (2013.01); *A61M 2205/6054* (2013.01); *A61M 2230/432* (2013.01); *A61M 2230/50* (2013.01); *A61M 2230/65* (2013.01)

(56) References Cited

U.S. PATENT DOCUMENTS

| | | |
|---|---|---|
| 9,750,461 B1 | 9/2017 | Telfort |
| 2012/0323086 A1* | 12/2012 | Hansen ................. G16H 40/63 600/301 |
| 2014/0245782 A1 | 9/2014 | Howard et al. |
| 2017/0119983 A1 | 5/2017 | Lindkvist |

\* cited by examiner

SYSTEMS AND METHODS FOR OPERATING AN ALERT SYSTEM OF MEDICAL DEVICES

CROSS-REFERENCE TO RELATED APPLICATION

The present application claims priority to and the benefit of U.S. Provisional Application No. 62/558,715, entitled "SYSTEMS AND METHODS FOR OPERATING AN ALERT SYSTEM OF MEDICAL DEVICES," filed Sep. 14, 2017, the content of which is incorporated herein by reference in its entirety for all purposes.

TECHNOLOGICAL FIELD

The present disclosure generally relates to medical systems and, more particularly, to systems and methods for disabling an alarm system in a medical system in order to prevent (e.g., reduce or block) false alarms during a medical procedure that is rendered to a subject.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Some medical systems include a medical device (for example, cannula, mask, nasal tubing, carbon dioxide [CO2] sampling device, physiological sensor, etc.) that is attached to a patient (for example to a face, nose, index finger, wrist, etc.) and by which a physiological parameter of the patient is monitored. Sometimes, a patient may accidentally remove or move the medical device from its intended location, causing false measurements of the patient's physiological parameter. Often, movement of the medical device is intentional, as a patient wearing or using the medical device moves it aside in order to be able, for example, to talk or to eat more comfortably.

Some medical systems are designed to output an alert when a monitored physiological parameter indicates a medical problem, or when their operation is compromised (e.g., gets interrupted). However, some medical systems may also output nuisance alerts as a result of false measurements, for example, due to accidental removal or movement of the medical device Nuisance alerts may be distracting to the medical staff and may result in inefficient medical care, for example.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

It would, therefore, be beneficial to provide a system (e.g., a nuisance alert preventing system) that can prevent (e.g., reduce or block) nuisance alerts in medical systems. For example, the system may include components that can be mounted in or on various medical devices to detect movement or removal of the medical devices from a medically operational point (MOP) on a body of a subject during a medical procedure, and components that are configured to prevent nuisance alerts by the related medical system whenever the system detects such movement or removal of the medical device. It would also be beneficial to provide a system that can trigger an alert when a medical device that delivers treatment to a patient ((for example oxygen or medication via a nebulizer, venturi mask, or the like) moves (e.g., unintentionally moves) or is removed from a MOP.

In some embodiments, a system to prevent nuisance alerts in a medical system, or to trigger an alert when this is justified, may include a position sensing unit configured to sense a displacement of a medical device from a medically operational point on a subject, and a signal processing circuit to output, based on the sensed displacement, a signal to enable an alert system of a medical system cooperating with the medical device when the displacement is less than a threshold value, and to output a signal to disable the alert system when the displacement is equal to or greater than the threshold value.

In some embodiments, an alert activation/deactivation system is provided for a medical system and may include a position sensing unit to sense a displacement of a medical device from a medically operational point on a subject, and a signal processing circuit to output, based on the sensed displacement, a signal to disable an alert system of a medical system cooperating with the medical device if the medical device is for sensing a physiological parameter of a subject during a medical procedure and the displacement is greater than a first threshold value, and to output a signal to enable the alert system when the medical device is for delivering treatment to the subject and the displacement is greater than a second threshold value. The medical device may be configured to deliver treatment (e.g., oxygen, medication, etc.) to the subject. The physiological parameter may be oxygen saturation level, heart pulse rate, blood pressure, electrocardiogram (ECG), temperature and impedance, to name a few.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but may nevertheless be a routine undertaking of design, fabrication, and manufacture for those of ordinary skill having the benefit of this disclosure. Further, the current embodiments may be implemented by one or more computer-processors that implement one or more machine-readable instructions stored on a tangible, non-transitory, machine-readable medium and/or by specialized circuitry designed to implement the discussed features.

During a medical procedure or at various other times, a medical device may be positioned at an intended location on the body of the patient. The intended location may be the location at which the medical device is usually attached in order to obtain optimal operation (e.g., generally desirable or effective operation) of the medical system as a whole, for example, in order to obtain optimal measurements (e.g., reliable or accurate measurements) of a physiological parameter and/or in order to provide optimal medical care (e.g., appropriate or intended medical care). The intended location is referred to herein as a medically operational point (MOP).

As noted above, some medical systems are designed to output an alert when a monitored physiological parameter indicates a medical problem, or when their operation is compromised (e.g., gets interrupted). However, some medical systems may also output nuisance alerts as a result of false measurements, for example, due to removal or movement of the medical device from the MOP. For example, a medical system monitoring a physiological parameter of a patient (e.g., oxygen saturation level in a subject, concentration level of exhaled $CO_2$, etc.) outputs an alert when the value of a measured, or sensed, physiological parameter is lower than a threshold. In another example, a capnography system is designed to normally output a $CO_2$ level alert when the concentration of $CO_2$ exhaled by the patient is lower than a threshold value. Continuing the examples, a patient may accidentally remove or move the cannula, or mask, through which the $CO_2$ monitoring system obtains $CO_2$ samples, from its medically operational point, thus causing a nuisance alert.

Figure 1:
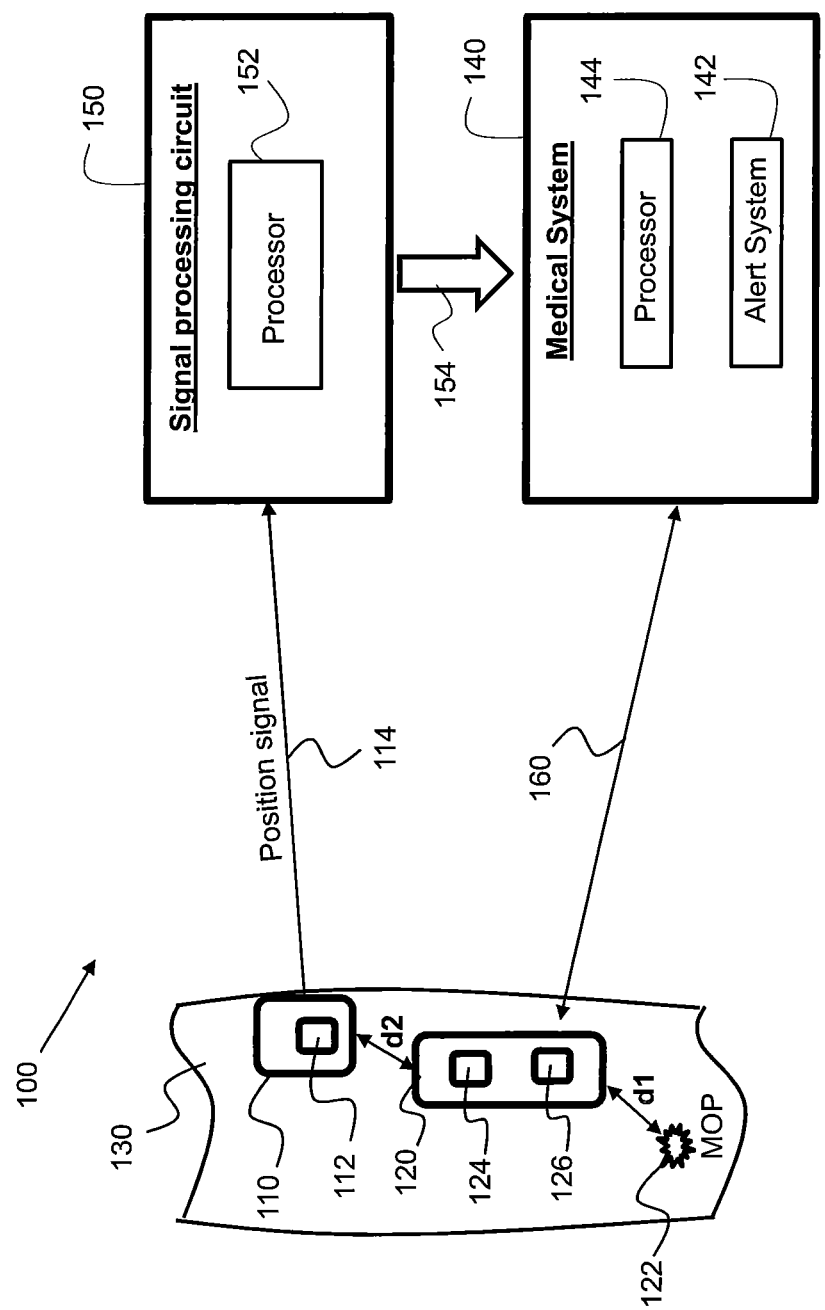
FIG. 1 schematically illustrates a nuisance alert preventing system, according to an embodiment of the present disclosure.

FIG. 1 schematically illustrates a nuisance alert preventing system 100 (e.g., nuisance alert blocking system) according to an example embodiment. Nuisance alert preventing system 100 may include a position sensing unit (PSU) 110. PSU 110 may include a position sensor 112 configured to output a signal 114 (e.g., a position signal) that represents a displacement d1 of a medical device 120 from a MOP 122 on a subject 130. Medical device 120 is configured to cooperate with a medical system 140 to perform a medical procedure. Nuisance alert preventing system 100 may also include a signal processing circuit (SPC) 150 that includes, among other things, a processor 152. Processor 152 may be configured to output 154, to medical system 140, based on position signal 114, a signal to enable an alert system 142 of medical system 140 when position signal 114 indicates a displacement d1 of medical device 120, which is smaller, less or lower than a threshold value, and to output a signal to disable alert system 142 when position signal 114 indicates an excess displacement, that is, a displacement d1 that is equal to or greater than the threshold value. In some embodiments, the value of displacement d1 may be set to a reference value (e.g., baseline, first, or initial value or position) that represents an optimal alignment (e.g., baseline, first, or initial alignment) of medical device 120 with MOP 122, and a deviation from the reference value of d1 may be interpreted (e.g., by medical system 140 or SPC 150) as misalignment, or displacement, of medical device 120 from MOP 122.

In some embodiments, a sensing facilitating means 124 (e.g., element detectable by position sensor 112) may be incorporated in or attached to medical device 120 and configured to facilitate sensing, by or in conjunction with position sensor 112, a displacement d1 of medical device 120 from MOP 122. For example, position sensor 112 may be or include a proximity sensor (e.g., switch), and sensing facilitating means 124 may be or include a metal body that is designed to change the state (on/off or open/closed) of the proximity sensor/switch as a function of the distance between the two devices. In some embodiments, sensing facilitating means 124 may be or include a miniature transponder (e.g., a radio frequency identification (RFID) tag/system) that may be designed to cooperate with position sensor 112 (that may be, in this example, a conjugated RFID reader) when the two devices are within a certain distance from one another. Briefly, an RFID system uses electromagnetic fields to automatically identify and track an RFID tag that is attached to an object. RFID tags contain electronically stored information. Passive RFID tags, for example, collect energy from interrogating radio waves transmitted from a nearby RFID reader. In some embodiments, position sensor 112 may be a proximity sensor/switch, and sensing facilitating means 124 may be, or include, in these embodiments, a metallic element as a target object to which the proximity sensor/switch reacts (e.g., by changing state from "close" to "open", and vice versa). It should be appreciated that in some embodiments, the position sensor 112 may be coupled to or incorporated into the medical device 120, while the sensing facilitating means 124 is a separate component that may be coupled to the subject 130 at a location at or near the MOP 122, for example.

Medical device 120 functionally cooperates 160 (e.g., via wireless or wired communication) with medical system 140 to perform a medical procedure. The medical procedure that medical system 140 may perform may be, for example, monitoring a physiological parameter which may be, for example, the concentration level CO2 of the CO2 exhaled by the subject, the oxygen saturation level in the subject's blood, the blood pressure of the subject, the heart pulse rate of the subject, electrocardiogram (ECG) monitoring by an ECG monitoring system, temperature, tissue impedance, etc. The medical procedure that medical system 140 may perform may be delivery of oxygen to the subject, administering medication to the subject, providing nutrition, etc. Cooperation 160 means that a processor 144 of medical system 140 may control transfer of oxygen and/or medication to the subject 130 via medical device 120, or that processor 144 may receive sensory signal(s) from medical device 120, which represent a physiological parameter(s) of the subject 130. Processor 144 may receive and process the signal 114 or the output 154 that is indicative of the position of the medical device 120 relative to the MOP 122 and, based on the processing result, processor 144 may enable or disable alert system 142.

Nuisance alert preventing system 100 may also include a signal processing circuit (SPC) 150. Signal processing circuit 150 may include a processor 152. Based on position signal 114, processor 152 may output 154, to or for medical system 140, a first signal to enable an alert system 142 of medical system 140 when position signal 114 indicates that medical device 120 and MOP 122 are aligned (for example, when position signal 114 indicates a relative displacement that is less than a threshold value). Based on position signal 114, processor 152 may also output 154 a second signal to medical system 140, to disable alert system 142 when the position signal 114 indicates that medical device 120 is misaligned with (e.g., displaced from) MOP 122 (for example, when position signal 114 indicates an excess displacement, that is, displacement that is equal to or greater than a threshold value).

Medical device 120 may be or include one or more of: a cannula, a nasal tubing, a face mask, a CO2 sampling device to collect exhaled CO2 for the CO2 monitoring system, an oxygen delivery device (e.g., mask, tube) to deliver oxygen to the subject, and a physiological parameter sensor (e.g., physiological parameter sensor 126) to sense a physiological parameter of the subject. Physiological parameter sensor 126 may be, for example, an oxygen sensor, a heart pulse rate sensor, a blood pressure sensor, a temperature sensor, ECG and an impedance sensor, to name a few. It should be appreciated that additional sensors may be used to sense different physiological parameters of the subject. In some embodiments, the first signal and the second signal that processor 152 of SPC 150 may output 154 are, respectively, to enable and disable alert system 142 of medical system 140 with respect to sensed values of the physiological parameter. In some embodiments, if, for example, medical device 120 is an oxygen delivery device, the first signal and the second signal that processor 152 of SPC 150 output 154 may, respectively, enable and disable alert system 142 in the related oxygen monitoring system 140 with respect to the delivery of oxygen to the subject.

Medically operational point (MOP) 122 on the subject may be selected from the group consisting of, for example: the face of the subject, the nose of the subject, the mouth of the subject, an index finger of the subject, a wrist of the subject, an elbow of the subject and the chest of the subject. In some embodiments, position sensor 112 may be positioned at a predetermined distance d2 from medical device 120, or position sensor 112 may be incorporated in or be attached to the medical device 120 (e.g., via a clip, fastener, tether, adhesive, or the like). In some embodiments, PSU 110, or only position sensor 112, is part of, incorporated in or attached to medical device 120. In some embodiments, SPC 150 is incorporated in medical system 140.

Position sensor 112 may be selected from the group consisting of, for example: an impedance sensor, a temperature sensor, a pressure sensor, a capacitive sensor, a proximity sensor, a motion sensor, an acceleration sensor and an optical sensor. Position signal 114 may be selected from the group of signals consisting of, for example: an electrical signal and a wireless signal. For example, PSU 110 may be wired to SPC 150, and position signal 114 may be transferred to signal processing circuit 150 via an electrical wire or cable. In another example, PSU 110 may use a radio frequency ("RF") communication circuit, for example a Bluetooth circuit, to transfer position signal 114 to SPC 150 wirelessly.

In some embodiments each one of PSU 110 and SPC 150 may include a communication modem (e.g., 344,374 FIG. 3) to enable the transfer of position signal 114 to SPC 150. As used herein, a modem may be a transmitter configured to wirelessly transmit signals, a receiver configured to wirelessly receive signals, or a transceiver configured to wirelessly transmit and receive signals to facilitate communication between components. In some embodiments, at least one of position sensor 112 and the communication modem of PSU 110 may be an add-on device that is attachable (e.g., removably attachable) to medical device 120, and thus, may be attached to the medical device 120 after manufacturing of the medical device 120 (e.g., at a clinical site prior to the medical procedure) and/or may be detached from the medical device 120 and attached to another medical device to enable reuse with multiple different medical devices 120. In some embodiments, at least one of position sensor 112 and the communication modem of PSU 110 may be embedded in medical device 120. In some embodiments, each communication modem is a bi-directional modem (e.g., modems 544 and 574, FIG. 5). In some embodiments, the communication modems are wireless. In some embodiments, the wireless modems are Bluetooth modems.

In some embodiments medical system 140 may be or include a CO2 monitoring system (e.g., system 200, FIG. 2), that is, a capnograph system, that is configured to measure CO2 concentration level (or another CO2-related parameter), or an oxygen delivery system to deliver oxygen to the subject, or an oximeter to measure oxygen saturation, or a heart pulse rate monitoring system to measure the subject's pulse rate, or an ECG system. "Capnography" is, in general, the monitoring of the concentration level or partial pressure of CO2 in the respiratory gases.

Figure 2:
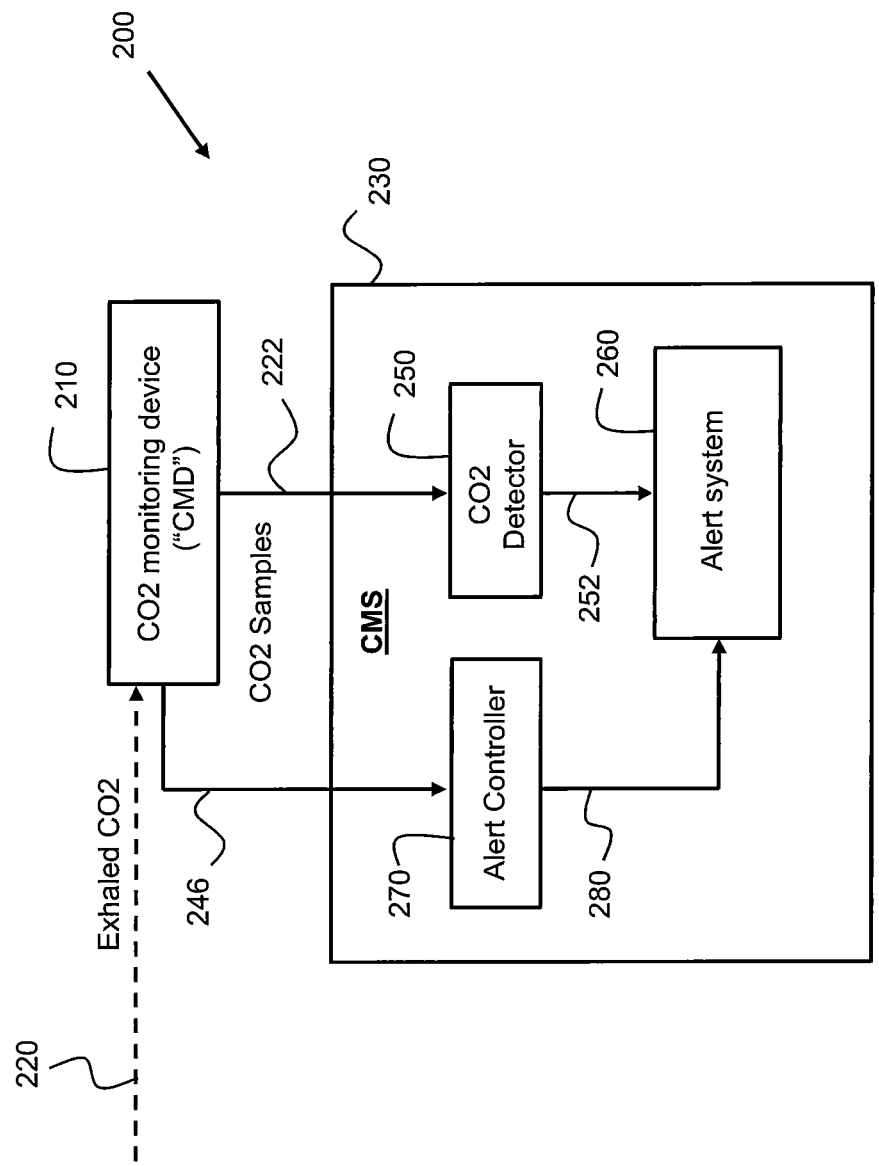
FIG. 2 schematically illustrates a CO2 monitoring system and a nuisance alert preventing system, according to an embodiment of the present disclosure.

In some embodiments, the first signal that processor 152 may output 154 to medical system 140 is configured (is an instruction or message) to enable normal operation of a CO2 alert circuit (e.g., CO2 alert circuit 260, FIG. 2) associated with the CO2 monitoring system (e.g., CO2 monitoring system 230, FIG. 2), and the second signal that processor 152 may output 154 to medical system 140 is configured (is an instruction or message) to disable the CO2 alert circuit (e.g., CO2 alert circuit 260, FIG. 2).

In some embodiments, the CO2 monitoring system (e.g., CO2 monitoring system 300, FIG. 3) may include a CO2 monitoring device (e.g., CO2 monitoring device [CMD] 310). The CMD (e.g., CMD 310) may include a CO2 sampling device (e.g., CO2 sampling device [CSD] 320, FIG. 3) as an example medical device. The CSD (e.g., CSD 320) may be designed, or it may include a device that is designed, to collect (e.g., 220, FIG. 2) CO2 samples of CO2 that is exhaled by the subject. For example, the device collecting the CO2 samples may be designed as a scoop or as a funnel. The CMD (e.g., CMD 310) may also include or be coupled to the PSU (e.g., PSU 340), which may be configured to output the position signal (e.g., 246, 346) that represents the position of the CO2 sampling device on the subject (e.g., position relative to the MOP and/or relative to a reference position). CO2 monitoring system 230 may be configured to receive 222, detect and process, by CO2 detector 250, the CO2 samples. Concurrently to CO2 detector 250 receiving 222 the CO2 samples, CO2 detector 250 receives, by alert controller 270, a position signal 246 from CO2 monitoring device 210 in order to determine whether the CO2 sampling device (e.g., CSD 320) was removed or moved from the designated MOP at the time when the related CO2 samples were collected by the CSD.

Carbon dioxide monitoring system 230 may be further configured to conditionally output, by alert system 260, an alert signal when a value associated with the processed CO2 samples exceeds a predetermined level or range, and the condition to output the alert signal is that the CO2 sampling device was not removed or moved from the MOP (that is, it is still at the MOP). Alert controller 270 processes position signal 246 in order to determine whether the CO2 sampling device has moved or been removed from the designated MOP, and outputs 280 to alert system 260 an "enable" or a "disable" signal according to the determination. In other words, CO2 monitoring system 230 is allowed to output an alert only if alert controller 270 determines (based on position signal 246) that the CO2 sampling device is still at (e.g., aligned with) the designated MOP; otherwise, alert controller 270 disables 280 alert system 260.

An example method of operating the system of FIG. 1 is described below. In some embodiments, PSU 110 may be attached to, or be positioned near or at, medical device 120. Medical device 120 may be positioned on, at or near medically operational point (MOP) 122 on subject 130. Once the medical device 120 and the PSU 110 are positioned in this manner, a reference value or a baseline position may be set. During patient monitoring, a change in the position of the medical device 120 relative to the MOP 122 may be detected via the PSU 110, and the change may be utilized to disable the alert system, for example.

Physiological parameter sensor 126 may sense a physiological parameter of subject 130, and transfer 160, to medical system 140, a parameter signal that represents the value of the physiological parameter. The parameter signal representing the value of the physiological parameter may be transferred 160 to medical system 140, for example, continuously, or according to a predetermined interval (for example, once every 10 seconds; however; other intervals may be used).

Processor 144 may process the parameter signal, or the information embodied in it, and, based on the value of the parameter signal (based on the information) which represents the physiological parameter, processor 144 may determine that alert system 142 should output or generate an alert due to the physiological parameter having abnormal value (s). However, concurrently to the monitoring of the physiological parameter, PSU 110, which uses position sensor 112, or position sensor 112 in conjunction with means 124, transfers position signal 114 to SPC 150 for processing, for example, by processor 152. Processor 152 may continuously, intermittently, or according to a predetermined time interval, determine from position signal 114 whether medical device 120 is at designated MOP 122, or whether medical device 120 is displaced from designated MOP 122 by an extent that renders measurements of the physiological parameter unreliable, which means that such measurements should be ignored and the alert system 142 disabled in order to prevent nuisance alert(s). Depending on the determination result, regarding enabling or disabling alert system 142, processor 152 may output 154 a corresponding instruction, or message, to processor 144 of medical system 140. In response to the instruction, or message, that processor 144 receives from processor 152, processor 144 may enable alert system 142 (allowing alert system 142 to output an alert), or disable it to prevent nuisance alerts when medical device 120 is displaced from MOP 122. SPC 150 may be external to medical system 140 or be part of (e.g., embedded in) medical system 140.

FIG. 2 schematically illustrates a system 200 in accordance with an example embodiment. System 200 may include a CO2 monitoring device (CMD) 210 and a CO2 monitoring system (CMS) 230. CMD 210 is configured to receive CO2 220 that is exhaled by a subject, to sample CO2 from the exhaled CO2, and to transfer 222, or to enable the transfer 222 of, the CO2 samples to CMS 230.

CMS 230 may include a CO2 detector 250 to detect the concentration level of, or another parameter related to, the CO2 samples. CO2 detector 250 may include a processor (the processor is not shown in FIG. 2). CO2 detector 250 (or the processor associated with it) may output an activation signal 252 to activate an alert system 260, which may be included in, for example, CMS 230, when the CO2 concentration level (or another parameter of the CO2 samples) has an abnormal value, for example, for a predetermined amount of time.

Concurrently with the transfer 222 of the CO2 samples to CMS 230, CMD 210 may transfer 246 a position signal to CMS 230. The position signal may represent the position of CMD 210 relative to a MOP on the body of the subject undergoing a CO2 monitoring procedure. In general, the location of a MOP depends on the medical procedure/monitoring being performed. If the medical procedure/monitoring being performed is CO2 monitoring, the MOP may be the subject's mouth and/or nose. That is, CMD 210 may be positioned at, or near, the subject's mouth and/or nose in a way that reliable CO2 measurements can be made.

Carbon dioxide monitoring system 230 may also include an alert controller 260 to which CO2 detector 250 (or the processor associated with it) may output the activation signal 252, and an alert controller 270. Alert controller 270 may analyze the position signal it receives 246 from CMD 210, and, based on the analysis result, may determine whether CMD 210 is still at, or operationally near, the designated MOP when CO2 samples are taken. If alert controller 270 detects (from the position signal) movement of CMD 210 away, or deviation, from the MOP, alert controller 270 outputs a signal 280 that disables alert system 260, so that if CO2 measurements are abnormal, the abnormal measurements are attributed to movement or removal of CMD 210 from the MOP, rather than these measurements indicating a genuine medical problem, and alert system 260 is, therefore, disabled.

If alert controller 270 detects (from the position signal) that CMD 210 is still at or operationally near the MOP, alert controller 270 outputs a signal 280 that enables alert system 260, so that if CO2 measurements are abnormal, the abnormal measurements are attributed to a genuine medical problem, and alert system 260 is, therefore, enabled.

Figure 3:
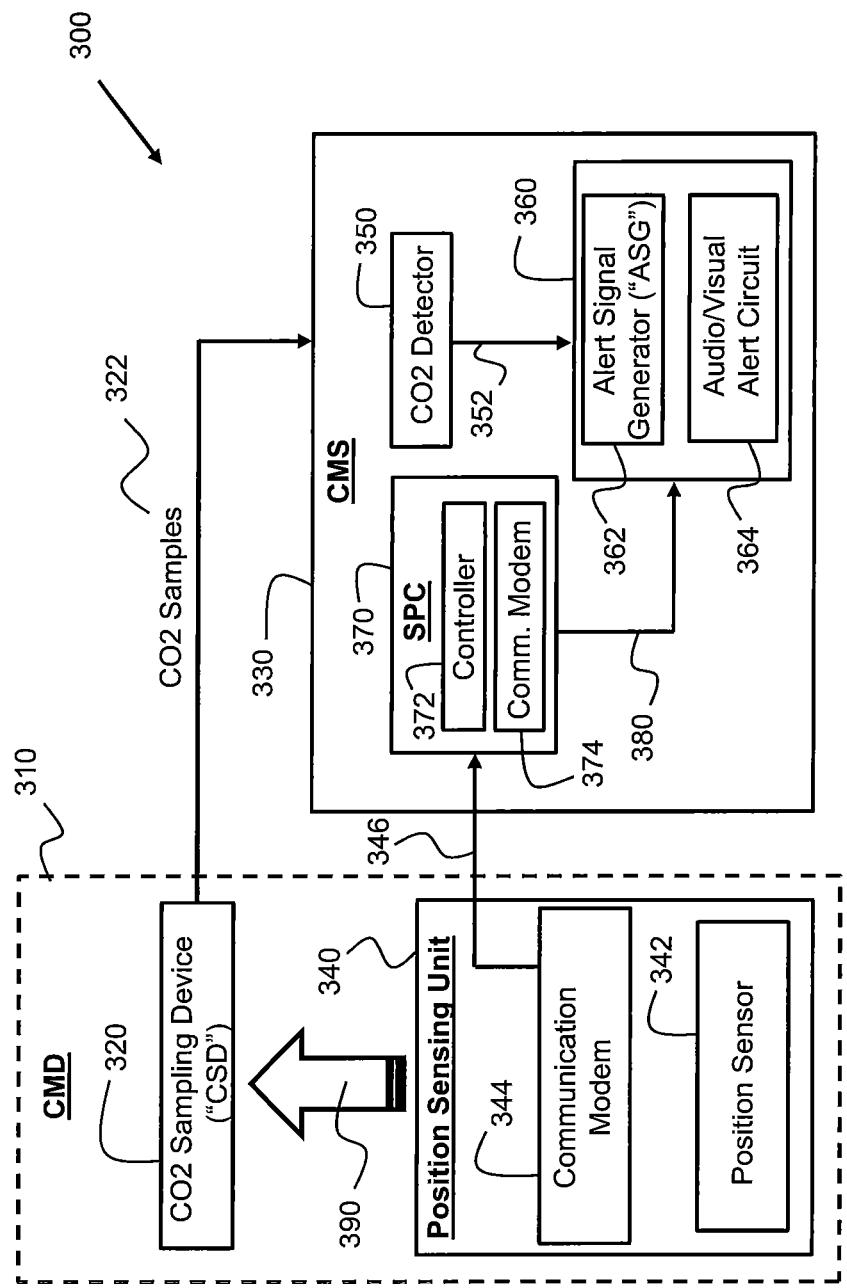
FIG. 3 schematically illustrates a CO2 monitoring system and a nuisance alert preventing system, according to an embodiment of the present disclosure.

FIG. 3 schematically illustrates a system 300 in accordance with an example embodiment. System 300 may include a CO2 monitoring device (CMD) 310 and a CO2 monitoring system (CMS) 330. CO2 monitoring device 310 may include a CSD 320 as an example medical device. CSD 320 may be configured to obtain samples from CO2 that is exhaled by a subject, and to transfer 322, or to enable the transfer of, the CO2 samples to CMS 330. It should be appreciated that CMS 330 may include a gas sampling pump to draw CO2 samples from CSD 320.

CO2 monitoring device 310 may also include a position sensing unit (PSU) 340. PSU 340 may include a position sensor 342 to sense the position of CSD 320 relative to a MOP on a body of the subject, and a communication modem 344 to transmit 346 the position signal to CMS 330. For example, in some embodiments, the CSD 320 may be initially positioned on the subject at the MOP, and the PSU 340 may establish or set this as a reference position for the CSD 320 (e.g., in response to a user input indicating that the CSD 320 is at the MOP, upon initiation of monitoring or therapy, or the like). Then, any subsequent movement away from the reference position may be detected by the PSU 340, and the PSU 340 may generate the position signal that indicates that the CSD 320 has moved relative to the MOP. Position sensor 342 may be entirely included in PSU 340, or only some components of position sensor 342 (for example, a controller, a power source, a signal processing/shaping circuit, etc.) may be incorporated in PSU 340, while other components of position sensor 342 (for example, a sensing electrode(s)) may be external to PSU 340 but operationally connected (for example, by being wired) to PSU 340.

CMS 330 may include a CO2 detector 350 to detect the concentration level of, or another parameter related to, the CO2 samples 322. CO2 detector 350 may include a processor (the processor is not shown in FIG. 3). CO2 detector 350 (or the processor associated with it) may output an activation signal 352 to activate an alert system 360, which may be included in, for example CMS 330, when the CO2 concentration level (or another parameter of the CO2 samples) has abnormal values, for example for a predetermined amount of time. Alert system 360 may include an alert signal generator 362 to generate an alert signal when CO2 detector 350 detects CO2 samples with abnormal values, and an audio-visual alert circuit 364 to effect the alert. CMS 330 may also include an alert system 360 and a signal processing unit (SPC) 370. SPC 370 may include a communication modem 374 to receive 346 the position signal from communication modem 344 of PSU 340, and a controller 372. Communication modem 344 may include a controller to process the output signal of position sensor 342, and to manage the transfer of position signal 346 to CMS 330.

Controller 372 may process the received 346 position signal and, based on the processed position signal, determine whether CSD 320 is still at, or operationally near, the designated MOP, or not. If CSD 320 is still at the designated MOP, or it is operationally near, the MOP (e.g., the displacement between the reference position and a current position is within a threshold value), controller 372 enables 380, or sets on or "arms," alert system 360 so that alert system 360 can operate normally or in a default operational mode (e.g., can go off) based on the signal 352 that CO2 detector 350 outputs regarding whether the measured CO2 samples indicate normal readings or abnormal readings. However, if CSD 320 is not at the designated MOP (e.g., the displacement between the reference position and a current position is not within a threshold value), controller 372 disables 380, or turns off, alert system 360 in order to prevent nuisance alerts. In some embodiments, PSU 340 may be releasably attached 390 to CSD 320, for example by using a snap fit connector or a snap fastener. SPC 370 may be external to medical system 330 or be part of (e.g., embedded in) medical system 330.

Figure 4A:
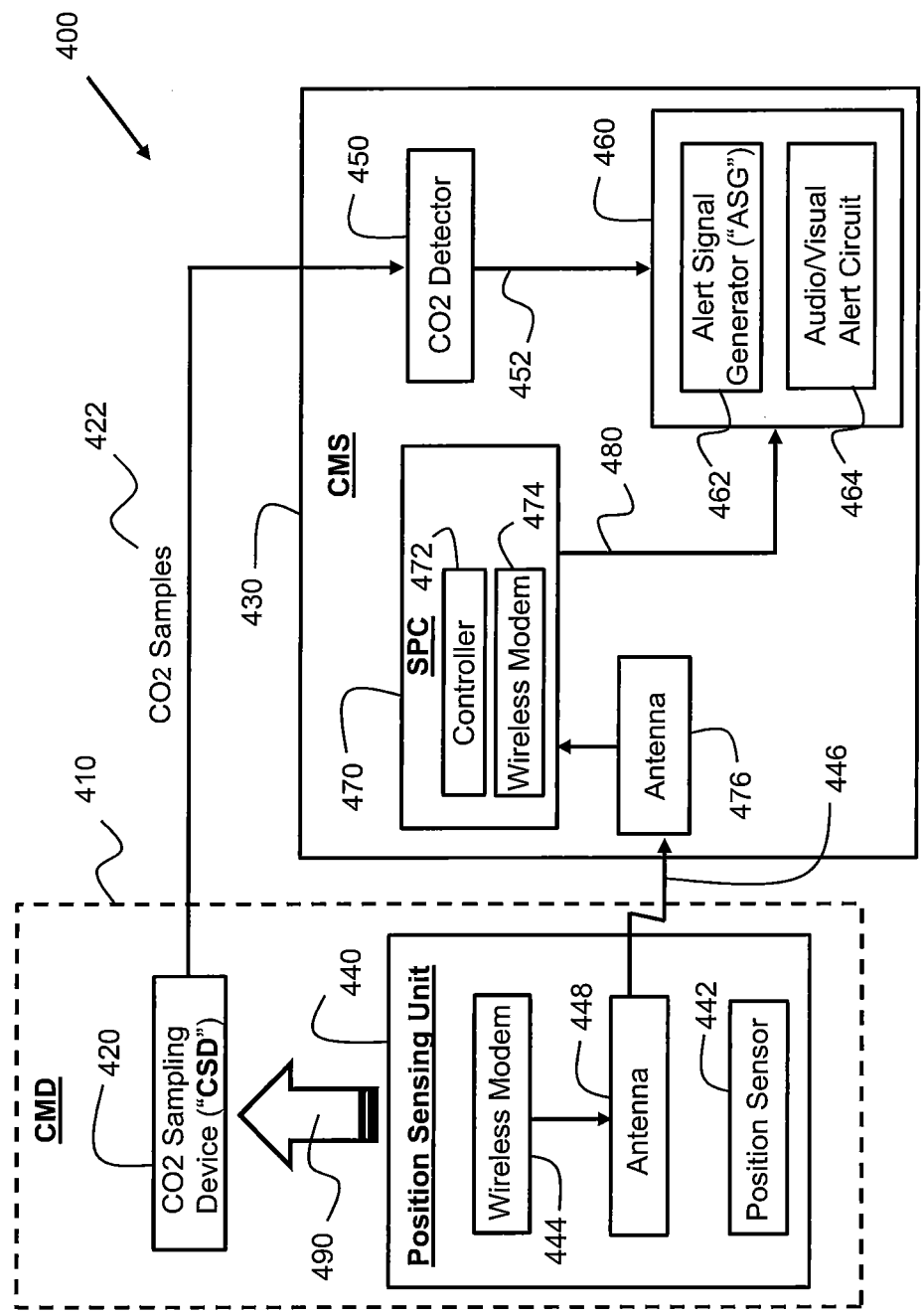
FIG. 4A schematically illustrates a CO2 monitoring system and a nuisance alert preventing system that wirelessly communicate with one another, according to an embodiment of the present disclosure.

FIG. 4A schematically illustrates a system 400 in accordance with an example embodiment. System 400 may include a CO2 monitoring device (CMD) 410 and a CO2 monitoring system (CMS) 430. CO2 monitoring device 410 may include a CO2 sampling device (CSD) 420 as an example medical device. CSD 420 may be configured to obtain samples from CO2 that is exhaled by a subject, and to transfer 422, or to enable the transfer of, the CO2 samples to CMS 430. It should be appreciated that CMS 430 may include a gas sampling pump to draw CO2 samples from CSD 420. CO2 monitoring device 410 may also include a PSU 440. PSU 440 may include a position sensor 442 to sense the position of CSD 420 relative to a MOP on the body of a subject, and a wireless communication modem 444 connected to an antenna 448 (e.g., radio frequency (RF) antenna) to wirelessly transmit 446, via antenna 448, the position signal to CMS 430. Position sensor 442 may be entirely included in PSU 440, or only some components of position sensor 442 (for example, a controller, a power source, a signal processing/shaping circuit, etc.) may be incorporated in PSU 440 while other components of position sensor 442 (for example, a sensing electrode(s)) may be external to PSU 440 but operationally connected (for example, by being wired) to PSU 440.

CMS 430 may include a CO2 detector 450 to detect the concentration level of, or another parameter related to, the CO2 samples 422 that are transferred to CMS 430 from CSD 420. Carbon dioxide detector 450 may include a processor (the processor is not shown in FIG. 4A). Carbon dioxide detector 450 (or the processor associated with it) may output an activation signal 452 to activate an alert system 460, which may be included in, for example CMS 430, when the CO2 concentration level (or the other measured parameter of the CO2 samples) has abnormal values, for example for a predetermined amount of time (e.g., for 10 seconds; however; other time periods may be used). Alert system 460 may include an alert signal generator (ASG) 462 to generate an alert signal when CO2 detector 350 detects, for example, CO2 samples with abnormal values, and an audio/visual alert circuit 464 to effect the alert. CMS 430 may also include a signal processing unit (SPC) 470. SPC 470 may include a wireless communication modem 474 to receive 446, via an antenna 476, the position signal from wireless communication modem 444 of PSU 440. SPC 470 may also include a controller 472. Communication modem 444 may include a controller to process the output signal of position sensor 442, and to manage the transfer of signal 446 to CMS 430. (The controller of communication modem 444 is not shown in FIG. 4A.)

Controller 472 may process the received 446 position signal and, based on the processed position signal, determine whether CSD 420 is still at, or operationally near, the designated MOP, or not. If CSD 420 is still at the designated MOP, or it is operationally near, the MOP (e.g., the displacement between the reference position and a current position is within a threshold value), controller 472 enables 480, or sets on or "arms", alert system 460 so that alert system 460 can operate normally or in a default operational mode (e.g., can go off) based on the signal 452 that CO2 detector 450 outputs regarding whether the measured CO2 samples indicate normal readings or abnormal readings. However, if CSD 420 is not at the designated MOP (e.g., the displacement between the reference position and a current position is not within a threshold value), or it has operationally displaced from, the MOP, controller 472 disables 480, or turns off, alert system 460 in order to prevent nuisance alerts. PSU 440 may be releasably attached 490 to CSD 320, for example by using a snap fit connector or a snap fastener.

In general, the location of a MOP, that may be, for example, a conspicuous point, area or feature on an organ, or an entire organ (for example a mouth, a nose, etc.) of, the subject, may be selected for initial or proper placement of the medical device by a medical professional depending, for example, on the medical procedure/monitoring being performed. For example, if the medical procedure/monitoring being performed is CO2 monitoring, the MOP may be, for example, the subject's mouth and/or nose (where reliable CO2 measurements can be made), and a deviation of the CSD (for example deviation of CSD 320 or CSD 420) may be detected with respect to the mouth and/or nose.

In some embodiments, enabling and disabling the alert system (e.g., alert system 360, alert system 460) may be effected by the CMS controller (e.g., controller 372, controller 472) sending the enable/disable signal (signal 380, signal 480) directly to the CO2 detector (e.g., CO2 detector 330, CO2 detector 430), for example to a controller that manages operation of the CO2 detector. In these embodiments, the CO2 detector (or its controller) may be allowed to output a "CO2 level low" (for example) alert signal (e.g., signals 352, 452) to set the alert system (e.g., alert system 360, alert system 460) off when the enable/disable signal (e.g., signals 380, 480) indicates that the medical device (for example CSDs 320, 420) is at, or operationally near, the designated MOP. Conversely, the CO2 detector (or its controller) may be inhibited from sending a "CO2 level low" (for example) alert signal (e.g., signals 352, 452) to the alert system (e.g., alert system 360, alert system 460) when the enable/disable signal (for example signals 380, 480) indicates that the medical device (for example CSDs 320, 420) is displaced (operationally moved away) from the designated MOP.

In some embodiments, enabling and disabling the alert system (e.g., system 360 or 460) may be effected by the communication modem of the PSU (e.g., modem 344 or 444), or a controller managing this modem, sending an enable/disable signal (e.g., signals 346, 446) (for example via a modem in the CMS; e.g., modem 374 or 474) to the CO2 detector (e.g., directly to detector 350 or 450), or directly to the alert system, to enable or to disable the alert system depending on whether the signal that the PSU (e.g., PSU 340 or 440) transfers to the CMS indicates that the medical device (for example, CSD 320 or 420) is operationally at or near the designated MOP. SPC 470 may be external to medical system 430 or be part of (e.g., embedded in) medical system 430.

Figure 4B:
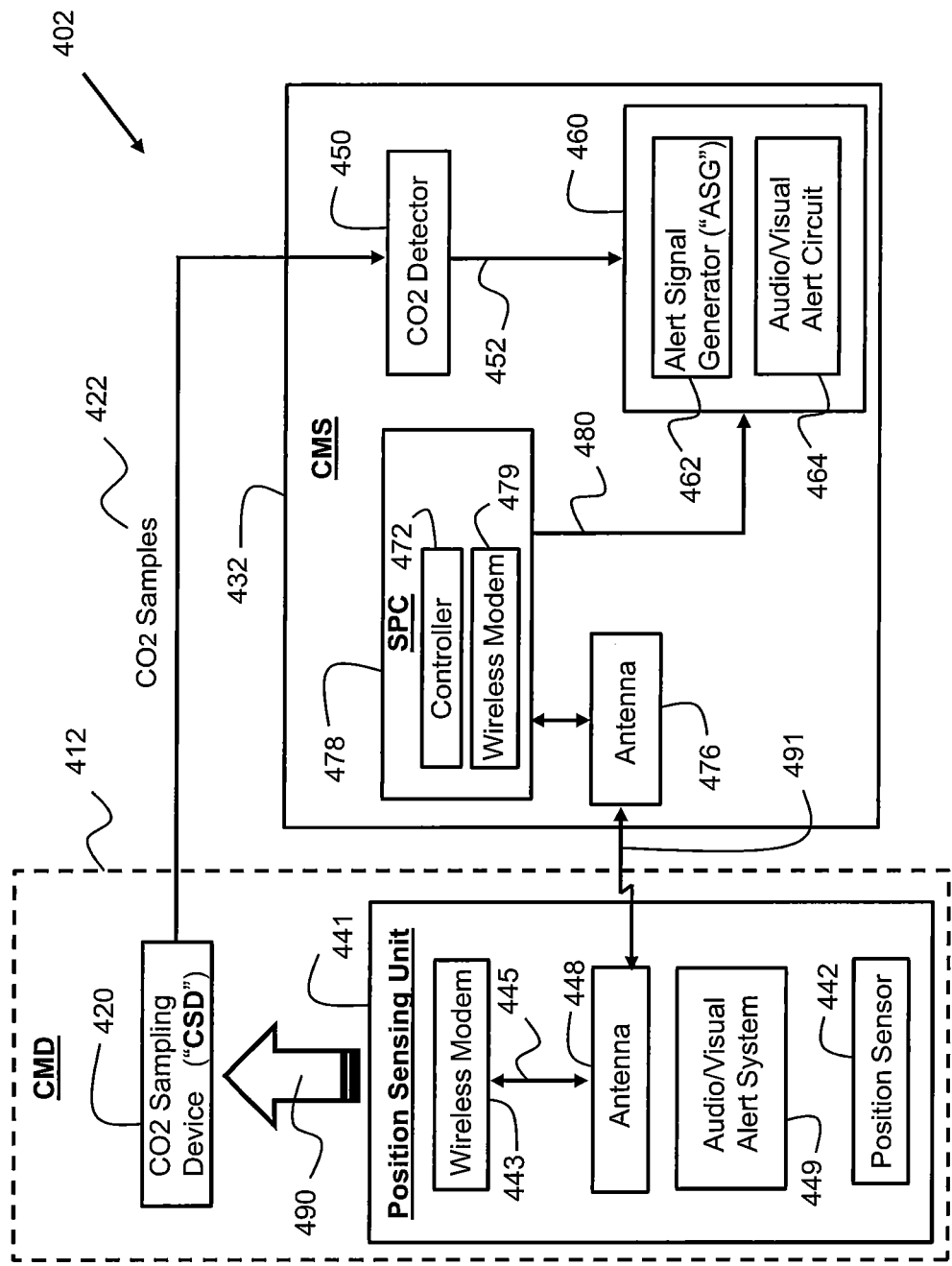
FIG. 4B schematically illustrates a nuisance alert preventing system having an audio/visual alert system associated with a position sensing unit, according to an embodiment of the present disclosure.

FIG. 4B schematically illustrates a system 402 in accordance with another example embodiment. Reference numerals are repeated among FIG. 4A and FIG. 4B to indicate like, corresponding or analogous elements, and, accordingly, the elements in FIGS. 4A and 4B that are referred to by the same reference numerals operate in a same way or in a similar way. Therefore, the way these elements operate is not described in connection with FIG. 4B.

System 402 may include a CMD 412 and a CMS 432. CMD 412 may include a CSD 420 as an example medical device, and a PSU 441. PSU 441 may include a wireless modem 443 which, in this example, is bidirectional modem that is capable of bidirectional communication with CMS 432. PSU 441 may also include an in-situ audio-visual alert system 449 to locally indicate (for example, to the subject wearing CSD 420) a displacement of CSD 420 (or another medical device) from a designated MOP. PSU 441 may also include an antenna 448 and a position sensor 442.

CMS 432 may include a CO2 detector 450, an alert system 460 and a signal processing unit (SPC) 478. SPC 478 may include a bidirectional wireless modem 479 to bidirectionally communicate with bidirectional wireless modem 443 via bidirectional communication path 491. SPC 478 may also include a controller 472 to control, among other things, the operation of communication modem 479. SPC 478 may be external to medical system 432 or be part of (e.g., embedded in) medical system 432.

PSU 441 and CMS 432 may exchange information with regard to activation, or deactivation, of an alert that is to be introduced (audibly and/or visually), or inhibited, in-situ (e.g., on CMD 412) or remotely (e.g., on CMS 432), as a result of a displacement of CSD 420. For example, exchanging information between PSU 441 and CMS 432 may include sending a disabling signal (491) from PSU 441 to CMS 432 to disable the CMS's alert system (460) so that low CO2 readings would not trigger an alert in CMS 432 when CSD 420 is not at the designated MOP, and sending CO2 measurements from CMS 432 to PSU 441 in order to trigger an in-situ alert signal by audio/visual alert system 449. In some embodiments, position sensor 442 may sense a displacement of CSD 420 from the designated MOP, and a controller managing the operation of PSU 441 may cause audio/visual alert system 449 to introduce (audibly or visually) an alert when such a displacement is sensed (e.g., displacement that exceeds a threshold value).

Figure 5:
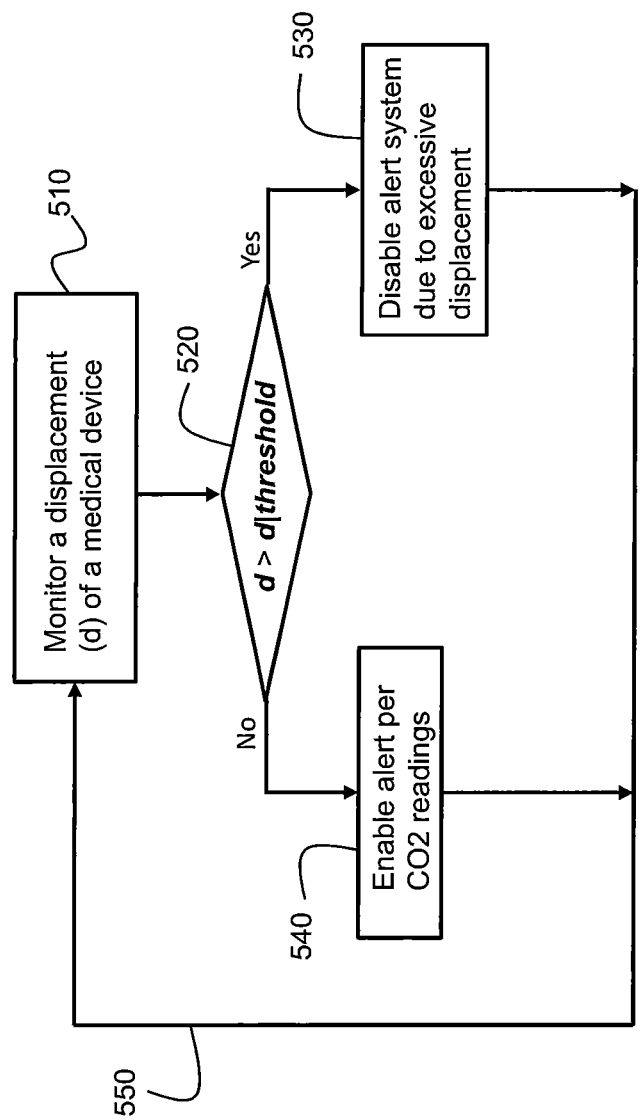
FIG. 5 shows a method for preventing nuisance alerts in medical system, according to an embodiment of the present disclosure.

FIG. 5 shows a method of disabling an alert system in a medical system monitoring a physiological parameter of a subject according to an example embodiment. By way of example, the method is described in connection with a CO2 monitoring system (CMS) as a medical system. However, a similar method may likewise be applied to other types of medical systems, for example it may be applied to an oxygen monitoring system, to an oxygen delivering system, to a heart pulse monitoring system, etc.

Initially, a medical device (e.g., CSD 420) may be positioned at a designated MOP of a subject to monitor a physiological parameter and/or to carry out a medical procedure. Then, while a subject's exhaled CO2 is sampled by a CO2 sampling device and monitored by a CO2 monitoring system, the following steps may be performed. At step 510, a displacement, d, of a medical device (e.g., CSD 420) used to sample exhaled CO2 from the designated MOP may be monitored by a PSU (e.g., PSU 440) continuously or once in a while (e.g., once every n seconds; n=1, 2, 3, . . . ). The PSU may send a position signal to the CMS. The position signal may be or represent the displacement, d. The PSU may monitor the displacement via any of a variety of techniques. For example, the PSU may establish a reference displacement value or a reference position while the medical device is positioned at the MOP (e.g., upon input by an operator indicating the medical device is positioned at the MOP, upon initiation of monitoring or the medical procedure, upon detection of the means 124, or the like). The PSU may then detect any subsequent movement or displacement of the medical device relative to the reference position, which may correspond to movement or displacement relative to the MOP. In some embodiments, the PSU may include one or more position sensors (e.g., position sensor 112) and one or more detectable elements (e.g., means 124). In some such cases, the position sensor may be placed at a first position on the subject and the detectable element may be coupled to or incorporated into the medical device, which may be placed at the MOP of the subject. The position sensor may then monitor for a change in a distance between the position sensor and the detectable element (e.g., the position sensor may be a proximity sensor that changes state when a distance between the position sensor and the detectable element exceeds a threshold value), which may be indicative of movement or displacement of the medical device relative to the MOP.

At step 520, a controller (e.g., a controller of the CMS) may compare the displacement d to a threshold value (d|threshold). If the displacement d is greater than the threshold value (if d>d|threshold, this condition is shown as "Yes" at step 520), the CMS's controller may, at step 530, disable an alert system of the CMS such that abnormal CO2 measurements would not set off the alert system of the CMS. However, if the displacement d is not greater than the threshold value (this condition is shown as "No" at step 520), the CMS's controller may, at step 540, enable the alert system of the CMS such that abnormal CO2 measurements would set off the alert system of the CMS. Monitoring the displacement of the medical device from the designated MOP may continue, as shown at step 550, or be repeated, for example, for as long as the physiological parameter (in this example, exhaled CO2) is monitored by the medical system (in this example, a CMS).

Figure 6A:
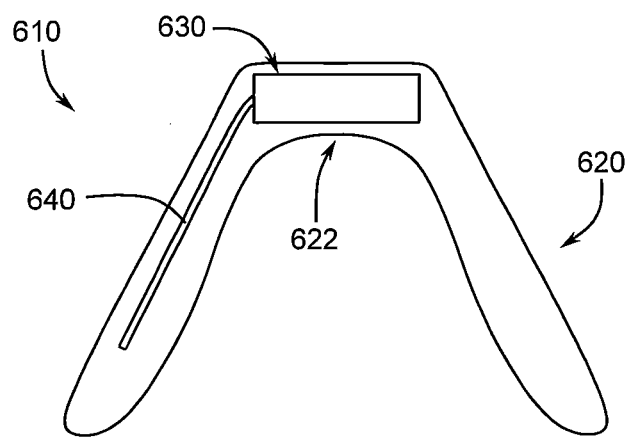
FIG. 6A shows a nose clip, according to an embodiment of the present disclosure.

In some embodiments, the medical device is a cannula. The cannula may be configured to collect samples of CO2 that is exhaled by a subject, and, in addition, it may be configured, in accordance with the present disclosure, to facilitate sensing of its own position with respect to a designated MOP. FIG. 6A depicts an example nose clip 610 according to an example embodiment. Nose clip 610 may include a V-shaped member 620 that is releasably attachable to the nose of a subject, for example in a similar way as an eyeglass's nose pad (by being lightly pressed against the nose). Member 620 may be an elongated member (e.g., clip) having a middle semi-straight segment (a bridge) 622 that bridges the two side segments of V-shaped member 620. Bridge section 622 may contain an electronic circuit 630. Electronic circuit 630 may be or include a PSU that may be identical or similar to, for example, PSU 420 (FIG. 4A).

The PSU may include a position sensor, a wireless communication modem and a controller to manage transmission of a position signal (that the position sensor outputs), for example, to a remote medical system. V-shaped (or U-shaped) member 620 may include an antenna 640 via which the PSU (e.g., its controller) may transmit the position signal. In some embodiments, the position sensor may be a proximity sensor (e.g., a proximity switch). The proximity sensor may be magnetic (inductive), capacitive, etc. A proximity switch is a device that causes a switching action without physical contact. In general, proximity switches respond to 'targets' that enter the active range of their generated sensing fields. Inductive proximity sensors, for example, are used for non-contact detection of metallic objects. Their operating principle of inductive proximity sensors is based on a coil and oscillator that creates an electromagnetic field in the close surroundings of the sensing surface.

Figure 6B:
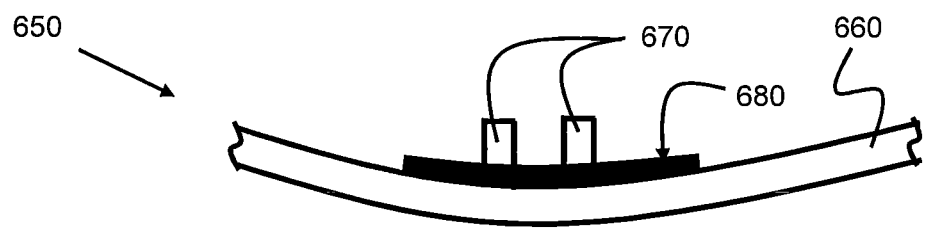
FIG. 6B shows a cannula, according to an embodiment of the present disclosure.

FIG. 6B depicts an example cannula 650 according to an example embodiment. Cannula 650 is used as an example medical device. It should be appreciated that the medical device subject of the present disclosure may be any medical device from a relatively simple device, for example, a tube, to a relatively complex device, for example, a face mask that enables both efficient delivery of oxygen to a subject via the mask, and concomitant extraction of exhaled CO2 from the mask. Cannula 650 may conventionally include a cannula tube 660 and prongs 670 (one prong per nostril). Prongs 670 may be used to deliver oxygen enriched air to a subject during respiration and/or to collect samples of CO2 that the subject exhales. Cannula 650 may also include an object 680 (e.g., a sensing target for a proximity sensor to sense or detect) in order for it to be sensed by the position sensor (e.g., proximity sensor coupled to or mounted on, for example, electric circuit 630). Object 680 may be, for example, metallic or ferromagnetic. In some embodiments, object 680 may be an RFID tag, and electric circuit 630 may include a RFID reader. The RFID reader may be configured to output a very low power radio frequency (RF) signal (e.g., a sensing signal) that is in compliance with the relatively small operational distance (e.g., gap) between the position sensor (e.g., in electric circuit 630) and, for example, cannula prongs 670 to enable the RFID reader to read the RFID tag when separated by the gap. When a distance between the RFID tag and the RFID reader exceeds the gap, the RFID reader may not read the RFID tag, thereby indicating that the RFID tag has moved away from the RFID reader and away from the MOP.

In some embodiments, the position sensor of nose clip 610 may be or include a light source (e.g., light emitting diode), a light guiding element (e.g., optical fiber) to guide light to a certain point on cannula 650, and a light sensor (e.g., photodiode) to sense a reflected light. In these embodiments, object 680 of cannula 650 may be or include a light reflecting element. The light source of the position sensor and the light reflecting element may be configured such that they are aligned (light is reflected back to the light sensor) when the cannula, or prongs, are at the designated MOP, and are misaligned when the cannula, or prongs, are displaced from the designated MOP, thereby enabling the electronic circuit 630 to monitor the position of the cannula relative to the designated MOP.

Figures 7A, 7B, 7C:
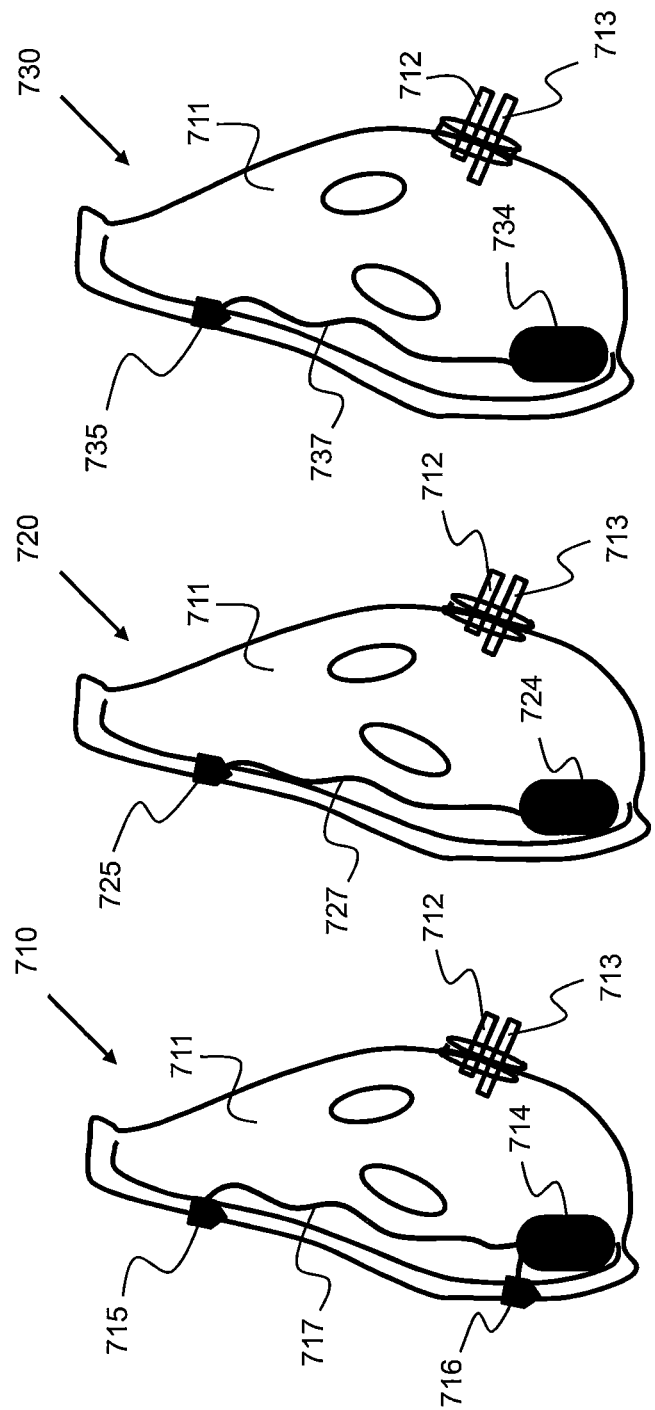
FIG. 7A illustrates an oxygen/capnography mask, in accordance with an embodiment of the present disclosure.
FIG. 7B illustrates an oxygen/capnography mask, in accordance with an embodiment of the present disclosure.
FIG. 7C illustrates an oxygen/capnography mask, in accordance with an embodiment of the present disclosure.

FIGS. 7A-7C schematically illustrate medical devices according to some embodiments. Referring to FIG. 7A, medical device 710, which is another example medical device, may include a face mask 711, an oxygen port 712 for delivering oxygen to a subject wearing face mask 711, and a CO2 port 713 through which samples of CO2 (which is exhaled by the subject) may be transferred from the interior space of mask 711 to a remote CO2 monitoring system. Medical device 710 may include only oxygen port 712, or only CO2 port 713, or both ports 712 and 713. In operation, mask 711 is positioned on the face of a subject such that delivery of oxygen to the interior space of the mask is optimal (e.g., maximized, desired, or adequate for treatment), and the sampling of the exhaled CO2 is also optimal (e.g., maximized, desired, or adequate for monitoring). Such optimal performance of the mask may be obtained when the mask is in an optimal position (e.g., desired, intended, or appropriate position) with respect to the subject's face, the optimal position being referred to herein as the medically operational position (MOP).

Medical device 710 also includes a position sensing unit (PSU) 714. PSU may 714 include an electric circuit that is connected to two electrodes (715, 716). Electric circuit 714 may include a controller and a wireless communication modern or transceiver. Electrodes 715 and 716 may be used to sense, for example, an impedance of a tissue that is contacted by mask 711. When the mask is removed from the subject's face, the impedance sensed between the two electrodes is expected to be infinite, and when the mask is moved on the subject's face, the impedance sensed between the two electrodes is expected to change or be unstable. Each electrode may be wired to electric circuit 714. In some embodiments, in operation, the PSU 714 may obtain a first impedance measurement (e.g., reference or baseline measurement) with the electrodes 715, 716 (e.g., upon input from an operator that the medical device 710 is position at the MOP, upon initiation of monitoring or therapy, or the like), and then monitor for a change in the impedance, which is indicative of movement of the medical device 710 relative to the MOP. For example, electrode 715 is connected to electric circuit 714 via electric wire 717. During operation, the PSU may use electrodes 715, 716 to produce a position signal that represents the position of the mask on the face of the subject, or a position signal that indicates whether the mask is in the right position (e.g., at, or operationally near, the MOP) or not. The PSU's controller may use the wireless communication modem to transmit the position signal to the remote $CO_2$ monitoring system and/or to the remote oxygen delivery system to enable or to disable the alert system, for example.

FIG. 7B shows a medical device 720 which is somewhat different than medical device 710, the difference being that the PSU (PSU 724) is connected to a temperature sensor 725, rather than to impedance electrodes. Temperature sensor 725 may sense the temperature of the subject's skin, which, under normal conditions, is expected to be higher than the room temperature. The electric signal that PSU 724 receives from temperature sensor 725 (e.g., via electrical wire 727) may be indicative of a position of the medical device 720 relative to the subject, and thus, to the MOP. For example, in operation, the PSU 724 may obtain a first temperature (e.g., reference or baseline measurement) from the temperature sensor 725 (e.g., upon input from an operator that the medical device 720 is position at the MOP, upon initiation of monitoring or therapy, or the like), and then monitor for a change in the temperature (e.g., a decrease, such as by more than 1, 2, 3, 4, 5, 10, or 15 percent), which may be indicative of movement of the medical device 720 away from the subject's skin and relative to the MOP. PSU 724 may transmit the signal to a remote medical system that operates with medical device 720 to enable or to disable the alert system, for example.

FIG. 7C shows a medical device 730 which is somewhat different than medical devices 710 and 720, the difference being that the PSU (PSU 734) is connected to an optical scanner 735. Optical scanner 735 may be designed and function in a similar way as an optical computer mouse. For example, the optical scanner 735 may include a light source, typically a light-emitting diode ("LED"), and a light detector, such as an array of photodiodes, that together are configured to detect movement of the optical scanner 735 relative to a surface, such as a surface of the subject's skin. The electric signal that PSU 734 receives from optical scanner 735 (e.g., via electrical wire 737) may be indicative of a position of the medical device 730 relative to the subject, and thus, to the MOP. PSU 734 may transmit the signal to a remote medical system that operates with medical device 730 to enable or to disable the alert system, for example.

In some embodiments, an alert activation/deactivation system is provided for a medical system and may include a PSU (for example, a PSU similar to PSU 110) to sense a displacement d1 of a medical device (for example a medical device similar to medical device 120) from a MOP (e.g., MOP 122) on a subject (e.g., subject 130), and a signal processing circuit (for example, a signal processing circuit similar to signal processing circuit 150) to output 154, based on the sensed displacement d1, a signal to disable an alert system (for example, an alert system similar to alert system 142) of the medical system (for example, a medical system similar to medical system 140) cooperating with the medical device if the medical device is for sensing a physiological parameter of a subject during a medical procedure and the displacement d1 is greater than a first threshold value, and, in other embodiments, to output a signal to enable an alert system when the medical device is for delivering a treatment to the subject and the displacement d1 is greater than a second threshold value. In some embodiments, the second threshold value may be different than and/or less than the first threshold value. The medical device may be configured to deliver any treatment to the subject, for example oxygen, nutrition, medication, etc. The physiological parameter may be, for example, concentration level of exhaled $CO_2$, oxygen saturation level, heart pulse rate, blood pressure, electrocardiogram (ECG), body temperature and tissue impedance, to name a few.

Various aspects of the embodiments disclosed herein are combinable with various types of medical devices. Although the discussion herein relates to cannulas and to face masks, embodiments of the disclosure are not limited in this regard. For example, the embodiments may, similarly, be incorporated or built into, or attached to, or mounted in or on any medical device, such as (but not limited to) a medical device that senses oxygen saturation in a subject, or exhaled $CO_2$, or a body temperature, or a heart pulse, or blood pressure, signal, or a medical device that deliver treatment (e.g., oxygen, medication) to a subject. The embodiments may, similarly, be incorporated or built into, or attached to, or mounted in or on any medical device that delivers, or facilitates delivery of, for example, oxygen, nutrition or medication, to name a few medical procedures that can be performed by various medical devices.

Figure 8B:
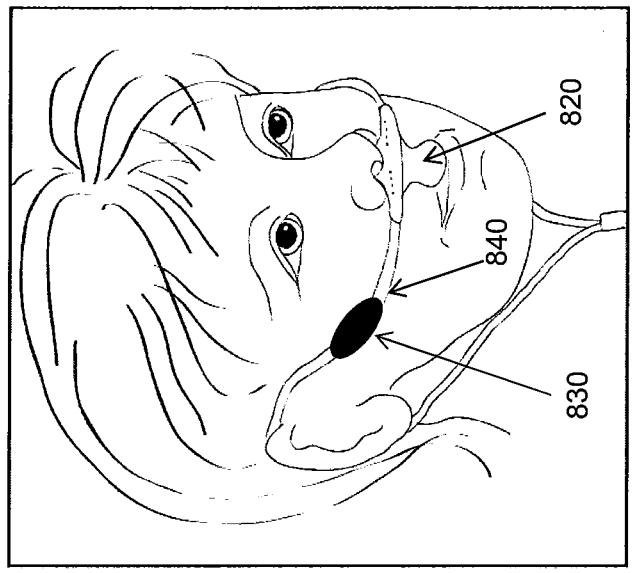
FIG. 8B illustrates a cannula in accordance with an embodiment of the present disclosure.
Figure 8A:
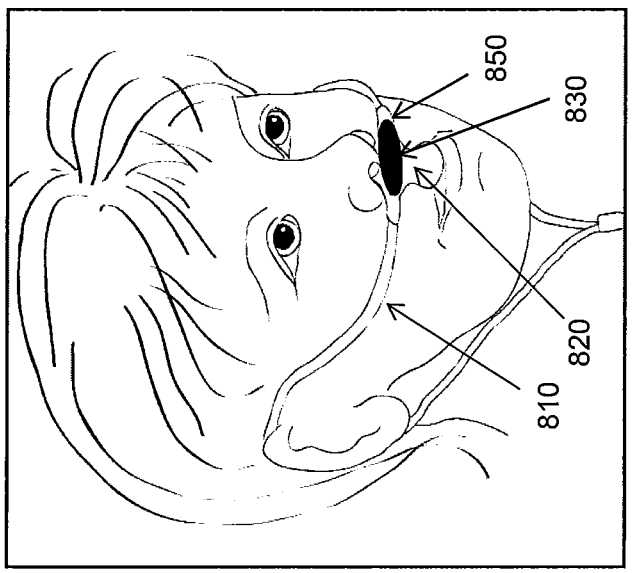
FIG. 8A illustrates a cannula, in accordance with an embodiment of the present disclosure.

FIGS. 8A-8B illustrate a cannula in accordance with some embodiments of the present disclosure. Referring to FIG. 8A, a cannula 810 includes a $CO_2$ sampling device (CSD, such as a scoop) 820 to collect samples of exhaled $CO_2$. Cannula 810 is mounted on a subject, and a position sensor unit (PSU) 830 is shown mounted on (e.g., releasably attached to) CSD 820. PSU 820 may be mounted on, or attached to, CSD 820 by using, for example, a snap fit connector, a snap fastener, or a Velcro strip. Alternatively, the PSU may be mounted on a side section or face section 840 of cannula 810, as shown in FIG. 8B at 830, instead of mounting the PSU (e.g., PSU 820) on the CSD (e.g., CSD 820), or on the cannula's mouth section 850 (as shown in FIG. 8A).

While certain features of the disclosure have been illustrated and described herein, many modifications, substitutions, changes, and equivalents will now occur to those of ordinary skill in the art, and the appended claims are intended to cover all such modifications and changes. It should be appreciated that the various features disclosed and illustrated in FIGS. 1-8B may be combined with one another in any suitable manner.

The invention claimed is:

1. A system to block nuisance alerts in a medical system, comprising:
    a position sensing unit configured to sense a displacement of a medical device from a medically operational point on a subject; and a signal processing circuit remote from the medical device and configured to output, based on the sensed displacement, a first signal to enable an alert system of a medical device cooperating with the medical system when the displacement is less than a threshold value, and to output a second signal to disable the alert system when the displacement is equal to or greater than the threshold value.

2. The system as in claim 1, wherein the position sensing unit comprises:
   a position sensor configured to output a position signal representing the displacement of the medical device from the medically operational point on the subject, wherein the medical device is configured to cooperate with the medical system to perform a medical procedure, and wherein the signal processing circuit comprises a processor that is configured to output for the medical system, based on the position signal, the first signal to enable the alert system of the medical system, and to output the second signal to disable the alert system.

3. The system as in claim 2, further comprising a first element incorporated in or attached to the medical device to facilitate sensing the displacement of the medical device from the medically operational point.

4. The system as in claim 1, wherein the medical device comprises: a cannula, a nasal tubing, a face mask, a $CO_2$ sampling device to collect exhaled $CO_2$ for the $CO_2$ monitoring system, and a physiological parameter sensor to sense a physiological parameter of the subject.

5. The system as in claim 4, wherein the physiological parameter sensor is selected from the group consisting of: an oxygen sensor, a heart pulse sensor, a blood pressure sensor, an electrocardiogram (ECG), temperature sensor, and an impedance sensor.

6. The system as in claim 1, wherein the medically operational point on the subject is selected from the group consisting of: a face of the subject, a nose of the subject, a mouth of the subject, a finger of the subject, a wrist of the subject, an elbow of the subject, and the chest of the subject.

7. The system as in claim 2, wherein the position sensor is configured to be positioned at a predetermined distance from the medical device or is incorporated in or attached to the medical device.

8. The system as in claim 2, wherein the signal processing circuit is incorporated in the medical system.

9. The system as in claim 2, wherein the position sensor is selected from the group consisting of: an impedance sensor, a temperature sensor, a pressure sensor, a capacitive sensor, a proximity sensor, a motion sensor, an acceleration sensor, and an optical sensor.

10. The system as in claim 2, wherein each of the position sensing unit and the signal processing circuit comprises a communication modem configured to transfer the position signal from the position sensing unit to the signal processing circuit.

11. The system as in claim 10, wherein any of the position sensor and the communication modem of the position sensing unit is an add-on device attachable to, or embedded in, the medical device.

12. The system as in claim 11, wherein each communication modem is wireless.

13. The system as in claim 1, wherein the medical system is a $CO_2$ monitoring system configured to measure $CO_2$ concentration, an oximeter configured to measure oxygen saturation level, a heart pulse rate monitoring system configured to measure the subject's pulse rate, a blood pressure monitoring system configured to measure the subject's blood pressure, or an electrocardiogram (ECG) monitoring system configured to monitor electrical activity of the subject's heart.

14. The system as in claim 13, wherein the first signal enables a $CO_2$ alert circuit of the $CO_2$ monitoring system and the second signal disables the $CO_2$ alert circuit.

15. The system as in claim 13, wherein the medical device is a $CO_2$ monitoring device, the $CO_2$ monitoring device comprising:
   a $CO_2$ sampling device configured to collect $CO_2$ samples exhaled by the subject;
   the position sensing unit configured to output the position signal representing a position of the $CO_2$ sampling device on the subject;
   the alert system configured to output an alert signal based on a detected $CO_2$ concentration; and
   the signal processing circuit configured to activate or deactivate the alert system based on the position signal,
   wherein the $CO_2$ monitoring system is configured to receive and process the $CO_2$ samples and to receive the position signal from the $CO_2$ monitoring device, and to conditionally output an alert signal when a value associated with the processed $CO_2$ samples exceeds a predetermined level or range, the condition to output said alert signal being that the $CO_2$ monitoring system interprets said position signal as the $CO_2$ monitoring device being properly positioned on or relative to a face of the subject.

16. An alert activation/deactivation system for a medical system, comprising:
   a position sensing unit configured to sense a displacement of a medical device from a medically operational point on a subject; and
   a signal processing circuit remote from the medical device and configured to output, based on the sensed displacement, a first signal to disable an alert system of a medical system cooperating with the medical device when the medical device is for sensing a physiological parameter of a subject during a medical procedure and the displacement is greater than a first threshold value, or to output a second signal to enable the alert system when the medical device is for delivering treatment to the subject and the displacement is greater than a second threshold value.

17. The system as in claim 16, wherein the medical device is configured to deliver oxygen or medication to the subject.

18. The system as in claim 16, wherein the physiological parameter is selected from the group consisting of: concentration level of exhaled carbon dioxide, oxygen saturation level, heart pulse rate, blood pressure, electrocardiogram (ECG), body temperature and tissue impedance.

19. A method for monitoring carbon dioxide ($CO_2$), comprising:
   generating a position signal representing a position of a $CO_2$ monitoring device relative to a medically operational point on a subject and measuring $CO_2$ exhaled by the subject by a $CO_2$ monitoring system; and
   disabling, by an alert controller, an alert system of the $CO_2$ monitoring system in response to receipt of the position signal by a signal processing unit remote from the $CO_2$ monitoring device, the signal indicating an excess displacement of the $CO_2$ monitoring device with respect to the medically operational point.

20. The method as in claim 19, wherein the step of disabling the alert system comprises activating an indication in or on the CO2 monitoring device to indicate displacement of the CO2 monitoring device from the medically operational point.

* * * * *